(12) United States Patent
Becker et al.

(10) Patent No.: US 6,613,539 B1
(45) Date of Patent: Sep. 2, 2003

(54) METHOD AND APPARATUS FOR SIMULTANEOUSLY TESTING A PLURALITY OF COMPOUNDS TO DETECT THEIR ACTIVITY

(75) Inventors: Katherine Becker, Ypsilanti, MI (US); John Scott Brussolo, Ypsilanti, MI (US)

(73) Assignee: Warner Lambert Company, Morris Plains, NJ (US)

( * ) Notice: Subject to any disclaimer, the term of this patent is extended or adjusted under 35 U.S.C. 154(b) by 1300 days.

(21) Appl. No.: 09/163,572

(22) Filed: Sep. 30, 1998

Related U.S. Application Data

(63) Continuation of application No. 08/972,705, filed on Nov. 18, 1997, now abandoned, which is a continuation of application No. 08/411,130, filed on Mar. 27, 1995, now abandoned.

(51) Int. Cl.$^7$ .................................................. C12Q 1/60
(52) U.S. Cl. .............................. 435/11; 435/5; 435/69.2
(58) Field of Search ............................ 435/11, 5, 69.2; 422/62; 436/809

(56) References Cited

U.S. PATENT DOCUMENTS

| | | | |
|---|---|---|---|
| 4,039,286 A | 8/1977 | Keller et al. | 23/230 R |
| 4,166,095 A | 8/1979 | Kling et al. | 422/67 |
| 5,281,540 A | 1/1994 | Merkh et al. | 436/530 |
| 5,446,207 A * | 8/1995 | Pomponi et al. | 568/633 |

FOREIGN PATENT DOCUMENTS

| | | |
|---|---|---|
| EP | 0063810 | 3/1982 |
| WO | WO9313423 | 7/1993 |
| WO | 9313423 | 8/1993 |
| WO | WO9320242 | 10/1995 |

OTHER PUBLICATIONS

Evans G. A., Physical Mapping of Complex Genomes by Cosmid Multiplex Analysis, Proc Natl Acad Sci, USA vol. 86, pp. 5030–5034, Jul. 1989.*
Use of fluorescent Cholesteryl Ester Microemulsions in Cholesteryl Ester Transfer Protein Assays J. of Lipid Research 34:1625–1634, (1993) C.L. Bisgaier et al.
J. Med. Chem. May 13, 1994 37:1384–1401 E.M. Gordon et al. Appls. of Combinatotial Technologies to Drug Discovery. 2. Combinatorial Organic Synthesis, Library Screening Strategies, and Future Directions.
J.Am. Chem. Soc. 115, No. 6, 1993 J.M. Kerr et al. Encoded Combinatorial Peptide Libraries Containing Non–Natural Amino Acids.
S. De Marie et al., *Journal of Clinical Mirobiology*, vol. 20, No. 2, 1984, pp. 255–258. Aug.
PCT International Search Report ? Related Application.
S. De Marie et al., *Journal of Clinical Microbiology*, vol. 20, No. 2,1984, pp. 255–258. Aug.
PCT International Search Report Related App.
J. Am. Chem. Soc. 1994, 116: 373–374 A Borchardt et al. Synthetic Receptor Binding Elucideated with an Encoded Combinatorial Library.
J. Med Chem. 1994, 37:1233–1251 M.A. Gallop et al. Applications of Combinatorial Technologies to Drug Discovery. 1. Background and Peptide Combinatorial Libraries.
Use of fluorescent cholesteryl Ester Microemulsions in Cholesteryl Ester Transfer Protein Assays J. of Lipid Research 34:1625–1634, (1993) C.L. Bisgaier et al.
J. Med. Chem. May 13, 1994 37:1385–1401 E.M. Gordon et al. Appls. of Combinatotial Technologies to Drug Discovery. 2. Combinatorial Organic Synthesis, Library Screening Strategies, and Future Directions.
J.Am. Chem. Soc. 115, No. 6, 1993 J.M. Kerr et al. Encoded Combinatorial Peptide Libraries Containing Non–Natural Amino Acids pp. 2529–2531.

* cited by examiner

*Primary Examiner*—Ralph Gitomer
(74) *Attorney, Agent, or Firm*—Reising, Ethington, Barnes, Kisselle, PC

(57) ABSTRACT

Described is a method of simultaneously testing a plurality of compounds for activity comprising the steps of: (a) placing a plurality of the compounds into at least two arrays, each having a plurality of test zones, with multiple compounds in each zone; (b) determining the location of each compound in each test zone; (c) subjecting the array to a testing screen; and (d) ascertaining those compounds that had a positive response to the testing screen. Also described are apparatus for performing simultaneous testing of a plurality of compounds in a plurality of arrays containing the compounds to be tested for their activity.

29 Claims, 5 Drawing Sheets

METHOD AND APPARATUS FOR SIMULTANEOUSLY TESTING A PLURALITY OF COMPOUNDS TO DETECT THEIR ACTIVITY

CROSS-REFERENCE TO RELATED APPLICATIONS

This application is a continuation of U.S. patent application Ser. No. 08/972,705, filed Nov. 18, 1997, now abandoned which is a continuation of U.S. patent application Ser. No. 08/411,130, filed Mar. 27, 1995, now abandoned.

TECHNICAL FIELD

The invention pertains to the field of testing of compounds to ascertain their activity. The invention is particularly concerned with the laboratory testing of large quantities of compounds in a rapid manner.

BACKGROUND ART

Many organizations, in particular pharmaceutical organizations, over many years have synthesized a number of compounds for various research projects. Accordingly therefore, a large collection of compounds have been collected which includes a database of their structures and chemical properties. Frequently, these compounds are screened for biological assays to ascertain the activity of a compound with respect to the assay. A previous method of delivering the compounds involved selecting small numbers of compounds and weighing out the individual samples which were then sent for a single screen. With the advent of automated screening technology, the delivery method became inadequate. A single screen could test hundreds of compounds in a day, while each technician dispensing samples could only deliver a few dozen in a day.

New equipment became available to speed up the testing techniques. One technique was to manually dispense estimated amounts of individual compounds into small tubes that fit into a 96-well plate format. While automated equipment could dissolve the samples and mix them into the reaction wells, they still required a very substantial period of time to go through a screening process. The problem still remained as to how to have the substantial numbers of compounds to be screened for various assays. Preparation of the testing plates and the testing of the compounds per se was extremely labor intensive. It had previously been estimated that it would take almost a year to test approximately 100,000 compounds following this approach.

PCT Publication No. WO93/13423, published Jul. 8, 1993, describes an automated analysis equipment and assay method for detecting cell surface protein and/or cytoplasmic receptor function. The publication teaches an automated measuring apparatus which can decrease substantial worker effort. The publication indicates that for each drug that needed to be screened, the materials were tested one by one, even though an automated apparatus permitted the rapid detection of activity for the compounds tested.

U.S. Pat. No. 5,281,540 teaches a test array for performing assays. A semi-automated biological sample analyzer is described for simultaneously performing a plurality of enzyme immunoassays for human IgE class antibodies specific to a panel of preselected allergens in each of a plurality of biological samples. The technique, while having multiple biological samples in a well, uses a coating of an elongated cellulosic body such as a strip of paper which will contact the multiple samples to ascertain which antibodies are specific for the coated allergens and which will then, in turn, bind to the appropriate bands or islands. The bands or islands are then analyzed for the presence of labeled antibodies. The technique describes testing done in a seriatim basis, namely, a number of samples, one after the other, even though multiple samples are present in a reaction vessel. The use of antibodies which bind to a specific sample is required for the system to be effective. The samples may be detected by use of optical reading capabilities.

Other patents that test multiple compounds in a seriatim fashion utilizing automated equipment are described in U.S. Pat. Nos. 4,039,286 and 4,166,095.

It is an object of the present invention to simultaneously test a plurality of compounds utilizing at least two separate arrays of the same collection of compounds in each array.

SUMMARY OF THE INVENTION

Described is a method of simultaneously testing a plurality of compounds for activity comprising the steps of:
(a) placing a plurality of the compounds into at least two arrays, each having a plurality of test zones, with multiple compounds in each zone;
(b) determining the location of each compound in each test zone;
(c) subjecting the array to a testing screen; and
(d) ascertaining those compounds that had a positive response to the testing screen.

Also described is an apparatus for simultaneously determining the activity of a plurality of compounds comprising:
(a) a first array of a plurality of test zones, each zone having an ability to contain a plurality of compounds to be tested;
(b) a second array of a plurality of test zones, each zone having an ability to contain a plurality of compounds to be tested;
(c) means for simultaneously testing the compounds in the test zones; and
(d) means for ascertaining which compound in each array has a positive response to a testing screen after it has been determined that a compound has tested positive or negative for the activity.

DESCRIPTION OF PREFERRED EMBODIMENTS

Figure 1:
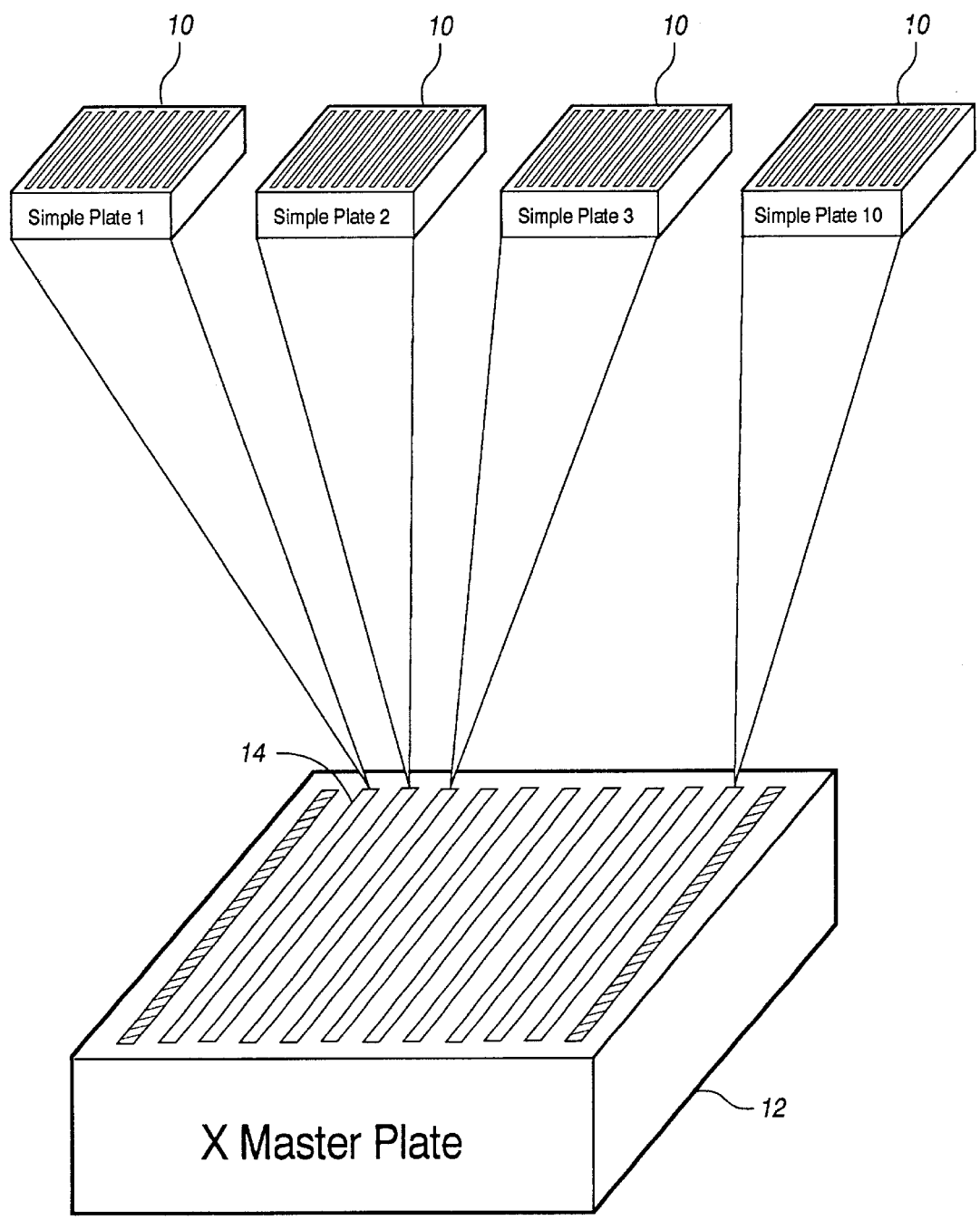
FIG. 1 is a schematic diagram showing the creation of the first array called an X plate utilized in the present invention.
Figure 2:
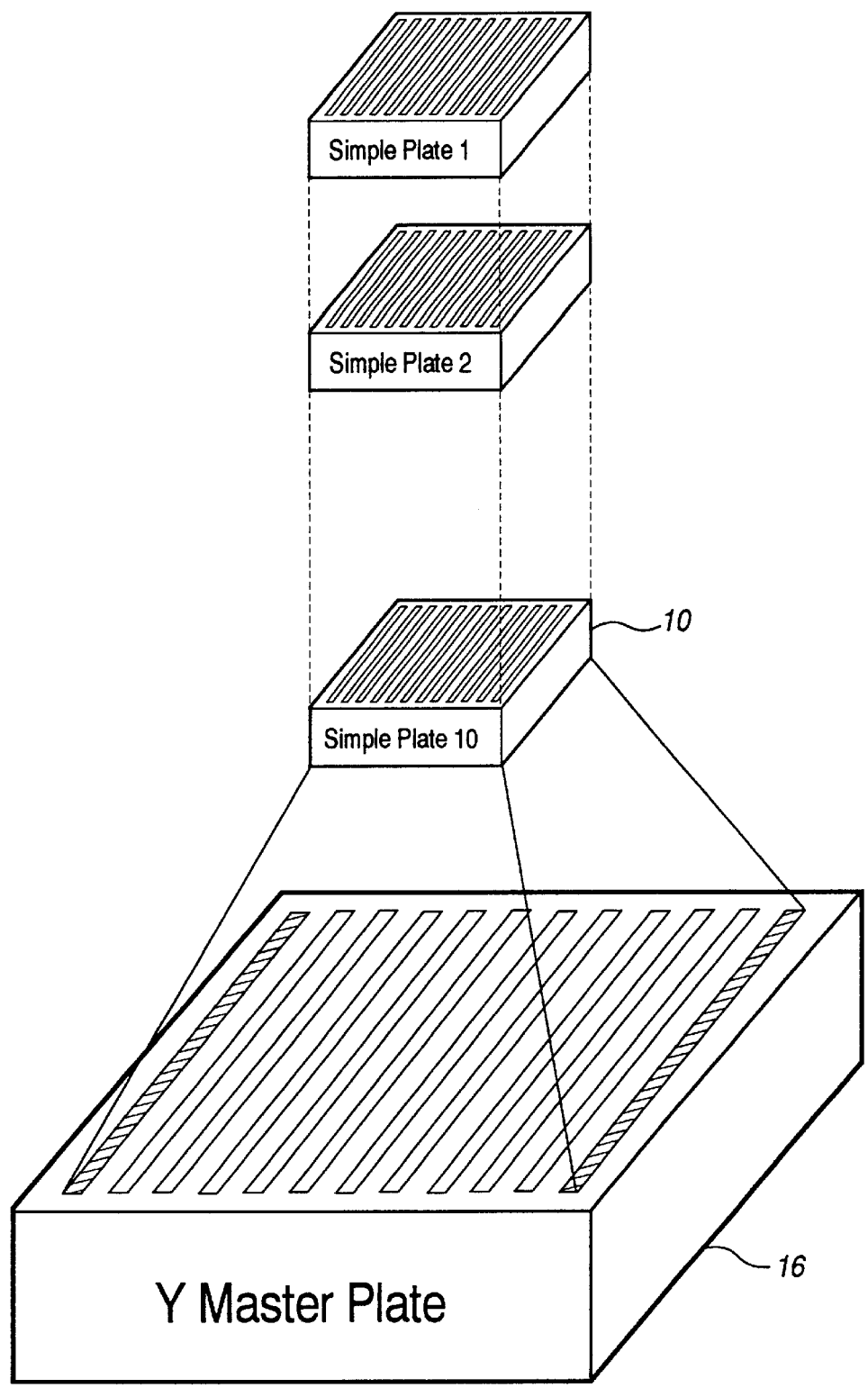
FIG. 2 is a schematic diagram showing the creation of the second array called a Y plate utilized in the present invention.
Figure 3:
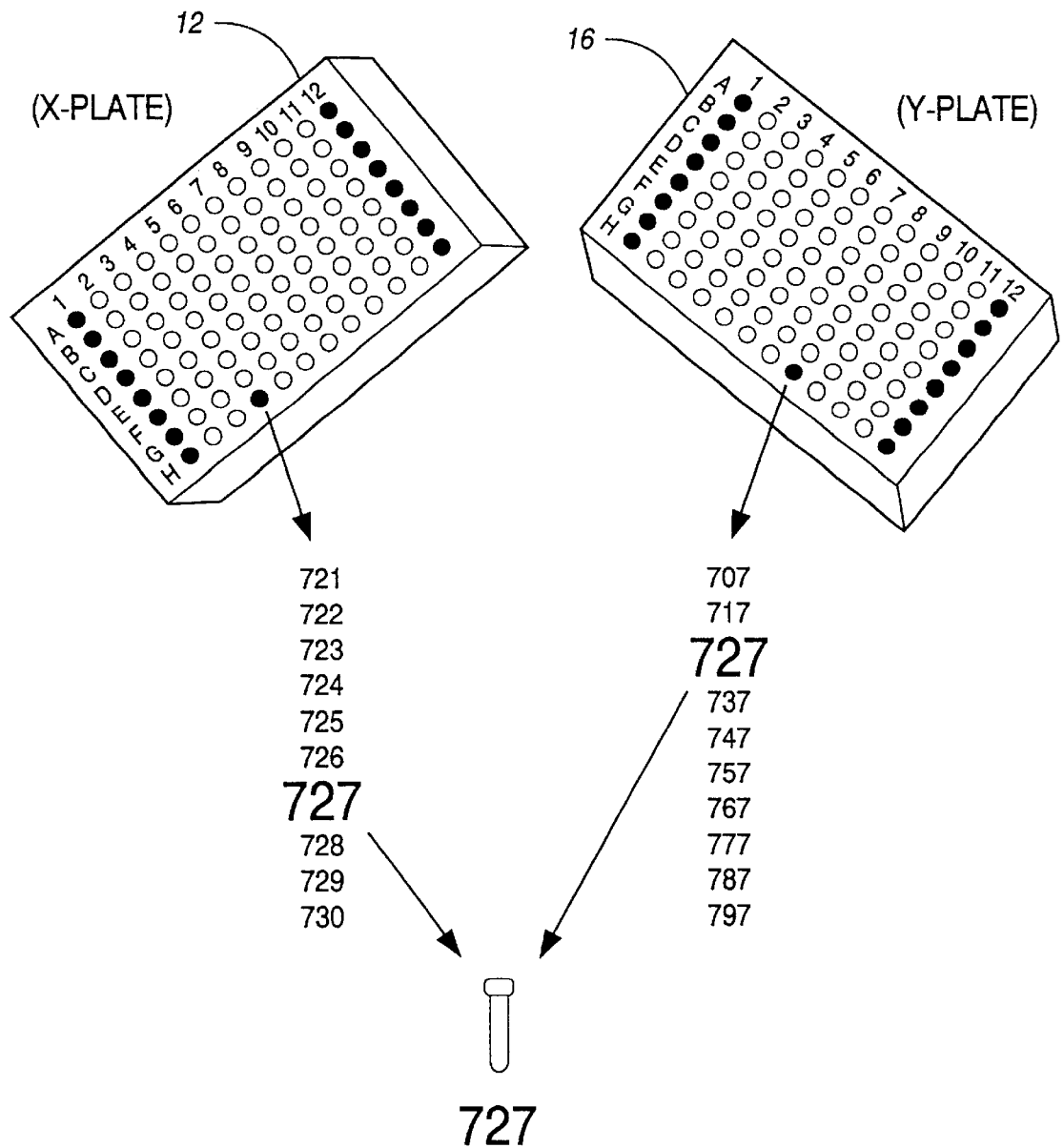
FIG. 3 is a schematic diagram depicting the utilization of FIGS. 1 and 2 in the mass screening techniques of the present invention using an orthogonal array.

The present invention can generally be characterized as a mass screening technique using an orthogonal array method (see FIG. 3). A simple plate (10) of FIGS. 1 and 2 utilizes ten columns across the top row A (of FIG. 3). The outermost columns (1 and 12 column numbers) are not used or are used for controls. Therefore, 80 compounds (8 rows of A–H with ten columns of 2–11) are placed into a 96-well plate called a "simple plate". The X master plate (12) is made up by placing an aliquot from each well from simple plate #1 into column 2 of the X master plate (14) and continued for the remainder of the ten simple plates.

The Y master plate (16) is prepared by taking the same contents of the ten simple plates (10) and placing the contents of each plate on top of each other so that the rows and columns of each simple plate fit within the test wells of the Y master plate (the rows and columns are the same for simple plate and Y master plate).

A master plate containing 800 compounds (the X Plate 12), such as a 96-well plastic plate, is prepared. A Y-Plate (16), identified as the orthogonal array master plate, likewise can contain 800 compounds. As can be seen from FIG. 3, if there is a compound that has activity such as hypothetical compound 727, it is present on the X Plate in well H4. On the Y Plate, it is found at well H8. Therefore, the activity has to correspond to a common compound, hypothetical compound 727 in this example. The method likewise is equally applicable for multiple active materials in a well.

In its most preferred feature, the current method is to make two plates that contain the same 800 compounds. One plate is the same as described above ("X Master plate"), and the other is arranged by turning the array of the first plate 90 degrees ("Y Master plate"). A Beckman robot was used to consolidate ten plates with one compound in each of 80 wells ("Simple Plate") using columns 2–11 and leaving columns 1 and 12 empty, into one plate with 10 compounds in each of 80 wells ("X Master plate") using columns 2–11 and leaving columns 1 and 12 empty (see FIG. 1). The consolidation begins by transferring a 50 μl aliquot from column 2 "Simple Plate" number one into column 2 of "X Master plate" number one, then transferring a 50 μl aliquot from column 3 "Simple Plate" number one into column 2 of "X Master plate" number one, etc., ending with transferring a 50 μl aliquot from column 11 "Simple Plate" number one into column 2 of "X Master plate" number one. The result is that an aliquot from each well of "Simple Plate" number one (10) exists in column 2 of "X Master plate" (12) number one (14). The same process is used for the remaining "Simple Plates" two through ten, such that an aliquot from each well of "Simple Plate" number two exists in column 3 of the "X Master plate", etc., ending with an aliquot from each well from "Simple Plate" number 10 existing in column 11 of the "X Master plate". The nature of the process ensures that every compound in row A of "Simple Plate" one through ten exists in row A of "X Master plate" number one, likewise through row H.

A Tomtec Quadra 96-100 (trademark of Tomtec, Inc. for automated well filling lab equipment) was used to consolidate each of the ten "Simple Plates" with one compound in each of 80 wells, into one plate with 10 compounds in each of 80 wells ("Y Master plate") using columns 2–11 and leaving columns 1 and 12 empty (FIG. 2). The consolidation begins by transferring a 50 μl aliquot from each of the 80 wells from "Simple Plate" number one into each of the 80 wells of "Y Master plate" number one, with the well location of the source "Simple Plate" matching the well location of the receiving "Y Master plate". This process continues for the remaining "Simple Plates" two through ten, such that an aliquot from each well of remaining simple plates is dispensed in the "Y Master plate", with the well location of the source "Simple Plate" matching the well location of the receiving "Y Master plate". The nature of the process ensures that every compound in row A of "Simple Plate" one through ten exists in row A of "Y Master plate" number one, likewise through row H. This process also ensures that the same 100 compounds are in row A of the "X Master plate" and in row A of the "Y Master plate", likewise through row H.

Figure 4:
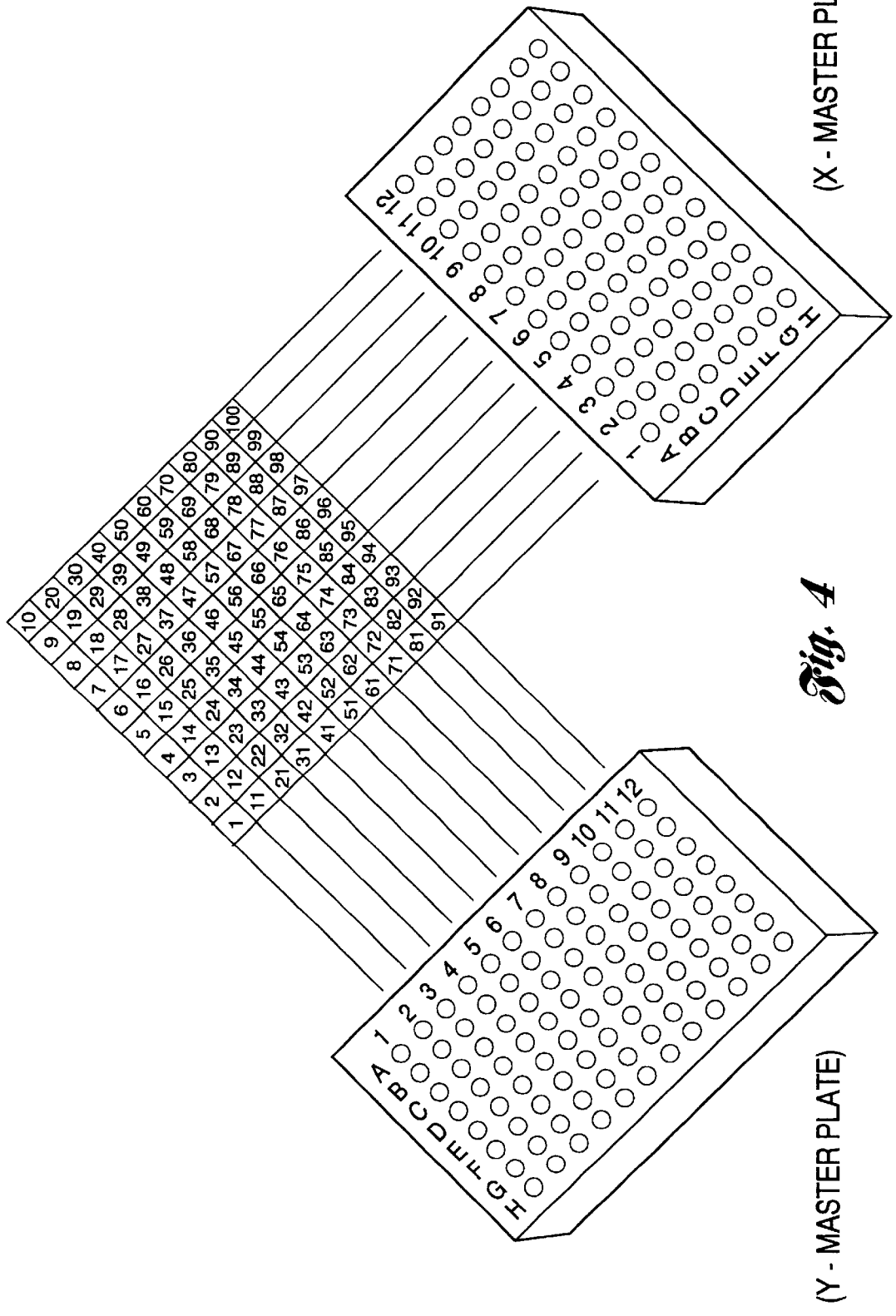
FIG. 4 is a combination array of a single row A of the X and Y master plates of FIGS. 1 and 2.

Both the "X Master plate" and the "Y Master plate" have 10 compounds in each well while each compound appears once on each plate. However, no two compounds have the same pair of well locations. When the plates are tested and the results compared, the individual compounds responsible for any activity can be determined. For convenience of assigning a location for each well, Applicant has devised an array combining the X and Y plates as shown in FIG. 4 which is an array of 10×10. For example, after testing "X Master plate" #1, well A2 is determined to be active (containing compounds 1 through 10, inclusive) and after testing "Y Master plate", well A11 is determined to be active (containing compounds 10, 20, 30, 40, 50, 60, 70, 80, 90 and 100). Only compound number 10 is common between the two wells determined to be active. Therefore, compound number 10 is assumed to be the active compound. FIG. 3 shows a similar hypothetical arrangement. If multiple wells are found in one row on one of the two plates and a single well is found on the corresponding row on the other plate, then one can ascertain the active compounds. For example, if, in addition to the active wells stated above, well A3 from the "X Master plate" is determined to be active (containing compounds 11 through 20, inclusive), then both compound number 10 and compound number 20 are common between the two plates. When multiple wells are determined to be active in the same row on both plates, then estimates may be made of the active material. That is, if well A2 and well A11 from both plates were determined to be active, then compounds number 1, 10, 91 and 100 would be derived from the orthogonal array. However, if only compound numbers 1 and 100 were active, the same four wells would show activity; likewise if only compound numbers 10 and 91 were active.

The advantage of this, even given the probability of testing inactive compounds, is that the biological testers can go directly to quantitative screening with individual compounds. There is no need to create plates that contain the individual compounds. The same plate pairs can be sent to multiple screens, without need to create differently arranged plates for each screen.

How to Identify the "Hit" Compounds From the X Y Plate Results

In this system, each row can be treated as a distinct entity. That is, any compound that is in row C on a simple plate, will also fall in row C on both the X plate and the Y plate. The same 100 compounds are in row C on both the X plate and the Y plate. There is no overlap between rows. So each master plate set actually carries eight completely separate 100 compound arrays.

Compounds in all types of plates are dissolved in DMSO (dimethyl sulfoxide), which means they can be transferred using pipeting rather than as solids, which makes it much easier to handle the mixing of very small amounts. However, for follow-up screening of the hit compounds, individual samples are weighed out dry from the sample collection. It is to be appreciated that any inert solvent may be used that is compatible with the testing screen. Such solvents include water, dimethyl formamide, N-methylpyrrolidone, glycols such as diethylene glycol, and the alkyl ether derivatives or the lower alkyl ester derivatives such as the Cellosolve solvents (trademark of Union Carbide).

Figure 5:
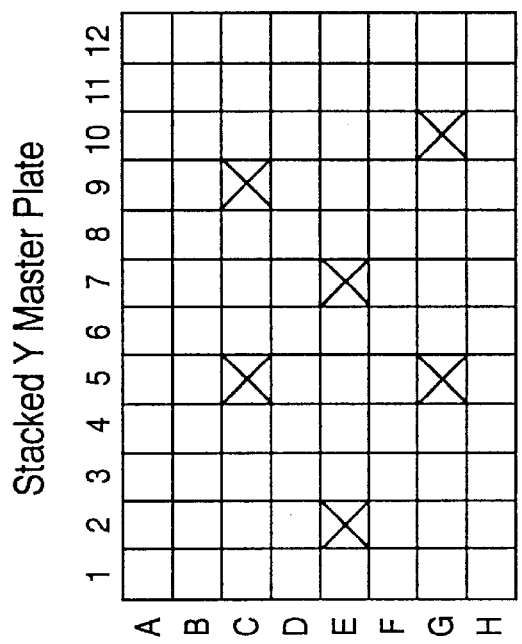
FIG. 5 is a master plate activity report showing hypothetical activity for the X and Y plates.
Figure 5:
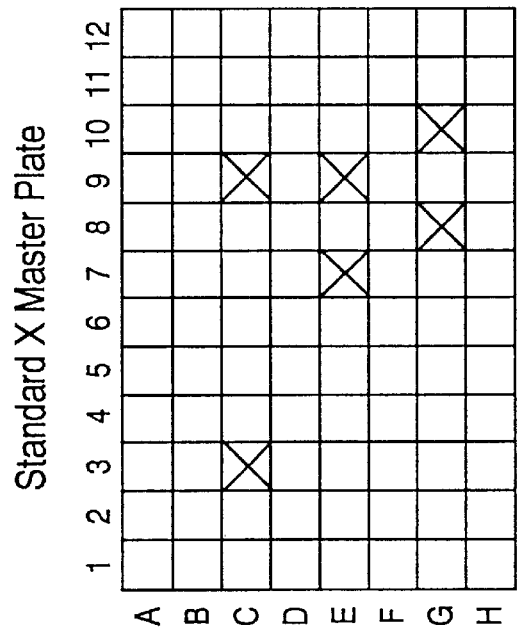

A Master Plate Activity Report (FIG. 5) shows the hypothetical test results on the X and Y master plates.

On the X plate report (20), in row C, there were two hits, in column 3 and in column 9. Now review the list of plate contents shown below in Table I.

Since the columns in the X plate were filled in order from left to right, with aliquots from simple plates in numerical order, we know that all ten compounds in well 3C on the X plate came from simple plate 1181, and they were all in row C. This narrows the choice to ten compounds from the content list, marked as "pink".

On the Y plate, in row C, there were also two hits, in columns 5 and 9. Turn to the list of plate contents again. Since the wells in the Y plate were all filled using aliquots from the same wells in the simple plates, we can scan the list of plate contents for all compounds in well 5C, in any simple plate, marked as "yellow".

Now compare the compounds that were marked. The only compound that was marked "pink" and "yellow", was in simple plate 1181, well 5C. The number of this compound is 108240.

When only one well is checked on each plate, in a given row, then its easy to narrow the hit to one compound. It is a little more complicated when two wells are checked on each plate, in a given row.

Look back at row C on the X plate. There were two boxes checked. Using the same method to locate all the compounds in the X plate's well 3C, the compounds in well 9C are marked as "green". All the compounds in the X plates' column 9 came from simple plate 1187. It is seen that one of these ten compounds is also marked as "yellow", because it was in well 5C in the Y plate.

Now look again at row C on the Y plate. There were two boxes checked there as well. The second box checked was 9C. Using the same method to locate all the compounds in the Y plate's well 5C, all the compounds from 9C have been marked as "blue". Each of the compounds in the Y plate's well 9C was also in well 9C on the simple plates it came from. It is seen that not only is one of these compounds marked as "green", there is also one that is marked as "pink".

So, there are four compounds that were marked twice. Therefore, four hits need to be followed up on. Each of the twice-marked compounds had one mark because it was in a Y plate hit well, and one mark because it was in an X plate hit well. The number of hits in a given row, is actually the product of the number of hits in that row in the X plate multiplied by the number of hits in that row in the Y plate.

TABLE I

| Plate No. | Col. | Row | Compound # Tested | |
|---|---|---|---|---|
| 1180 | 2 | A | 100001 | |
| 1180 | 2 | B | 100002 | |
| 1180 | 2 | C | 100003 | |
| 1180 | 2 | D | 100004 | |
| 1180 | 2 | E | 100005 | |
| * * * | | | | |
| 1180 | 4 | G | 107917 | |
| 1180 | 4 | H | 107918 | |
| 1180 | 5 | A | 107921 | |
| 1180 | 5 | B | 107923 | |
| 1180 | 5 | C | 107924 | Yellow |
| 1180 | 5 | D | 107934 | |
| 1180 | 5 | E | 107935 | |
| * * * | | | | |

TABLE I-continued

| Plate No. | Col. | Row | Compound # Tested | |
|---|---|---|---|---|
| 1180 | 9 | A | 108022 | |
| 1180 | 9 | B | 108031 | |
| 1180 | 9 | C | 108037 | Blue |
| 1180 | 9 | D | 108050 | |
| * * * | | | | |
| 1181 | 2 | A | 108145 | |
| 1181 | 2 | B | 108147 | |
| 1181 | 2 | C | 108151 | Pink |
| 1181 | 2 | D | 108154 | |
| 1181 | 2 | E | 108160 | |
| * * * | | | | |
| 1181 | 3 | A | 108169 | |
| 1181 | 3 | B | 108171 | |
| 1181 | 3 | C | 108172 | Pink |
| 1181 | 3 | D | 108174 | |
| 1181 | 3 | E | 108175 | |
| * * * | | | | |
| 1181 | 4 | A | 108190 | |
| 1181 | 4 | B | 108194 | |
| 1181 | 4 | C | 108197 | Pink |
| 1181 | 4 | D | 108200 | |
| 1181 | 4 | E | 108206 | |
| * * * | | | | |
| 1181 | 5 | A | 108238 | |
| 1181 | 5 | B | 108239 | |
| 1181 | 5 | C | 108240 | Pink-Yellow |
| 1181 | 5 | D | 108241 | |
| 1181 | 5 | E | 108242 | |
| * * * | | | | |
| 1181 | 6 | B | 108255 | |
| 1181 | 6 | C | 108259 | Pink |
| 1181 | 6 | D | 108261 | |
| 1181 | 6 | E | 108268 | |
| * * * | | | | |
| 1181 | 7 | A | 108290 | |
| 1181 | 7 | B | 108295 | |
| 1181 | 7 | C | 108296 | Pink |
| 1181 | 7 | D | 108302 | |
| 1181 | 7 | E | 108306 | |
| * * * | | | | |
| 1181 | 8 | B | 108331 | |
| 1181 | 8 | C | 108332 | Pink |
| 1181 | 8 | D | 108334 | |
| 1181 | 8 | E | 108335 | |
| * * * | | | | |
| 1181 | 9 | B | 108355 | |
| 1181 | 9 | C | 108357 | Blue-Pink |
| 1181 | 9 | D | 108366 | |
| 1181 | 9 | E | 108379 | |
| * * * | | | | |
| 1181 | 10 | B | 108418 | |
| 1181 | 10 | C | 108426 | Pink |
| 1181 | 10 | D | 108428 | |
| 1181 | 10 | E | 108433 | |
| * * * | | | | |
| 1181 | 11 | B | 108445 | |
| 1181 | 11 | C | 108446 | Pink |
| 1181 | 11 | D | 108451 | |
| 1181 | 11 | E | 108452 | |
| * * * | | | | |
| 1182 | 5 | A | 108569 | |
| 1182 | 5 | B | 108571 | |
| 1182 | 5 | C | 108578 | Yellow |
| 1182 | 5 | D | 108585 | |
| * * * | | | | |
| 1182 | 9 | A | 108769 | |
| 1182 | 9 | B | 108771 | |
| 1182 | 9 | C | 108779 | Blue |
| 1182 | 9 | D | 108788 | |
| * * * | | | | |
| 1183 | 5 | A | 109116 | |
| 1183 | 5 | B | 109125 | |
| 1183 | 5 | C | 109126 | Yellow |
| 1183 | 5 | D | 109132 | |
| * * * | | | | |
| 1183 | 9 | A | 109271 | |

TABLE I-continued

| Plate No. | Col. | Row | Compound # Tested | |
|---|---|---|---|---|
| 1183 | 9 | B | 109272 | |
| 1183 | 9 | C | 109277 | Blue |
| 1183 | 9 | D | 109278 | |
| | | | * * * | |
| 1184 | 5 | A | 109509 | |
| 1184 | 5 | B | 109510 | |
| 1184 | 5 | C | 109511 | Yellow |
| 1184 | 5 | D | 109513 | |
| | | | * * * | |
| 1184 | 9 | A | 109659 | |
| 1184 | 9 | B | 109666 | |
| 1184 | 9 | C | 109667 | Blue |
| 1184 | 9 | D | 109672 | |
| | | | * * * | |
| 1185 | 5 | A | 109933 | |
| 1185 | 5 | B | 109940 | |
| 1185 | 5 | C | 109941 | Yellow |
| 1185 | 5 | D | 109942 | |
| | | | * * * | |
| 1185 | 9 | A | 110082 | |
| 1185 | 9 | B | 110089 | |
| 1185 | 9 | C | 110096 | Blue |
| 1185 | 9 | D | 110097 | |
| | | | * * * | |
| 1186 | 5 | A | 110270 | |
| 1186 | 5 | B | 110272 | |
| 1186 | 5 | C | 110275 | Yellow |
| 1186 | 5 | D | 110276 | |
| | | | * * * | |
| 1186 | 9 | A | 110420 | |
| 1186 | 9 | B | 110421 | |
| 1186 | 9 | C | 110422 | Blue |
| 1186 | 9 | D | 110423 | |
| | | | * * * | |
| 1187 | 2 | A | 110525 | |
| 1187 | 2 | B | 110527 | |
| 1187 | 2 | C | 110529 | Green |
| 1187 | 2 | D | 110538 | |
| | | | * * * | |
| 1187 | 3 | A | 110567 | |
| 1187 | 3 | B | 110568 | |
| 1187 | 3 | C | 110582 | Green |
| 1187 | 3 | D | 110584 | |
| | | | * * * | |
| 1187 | 4 | A | 110595 | |
| 1187 | 4 | B | 110596 | |
| 1187 | 4 | C | 110598 | Green |
| 1187 | 4 | D | 110604 | |
| | | | * * * | |
| 1187 | 5 | A | 110612 | |
| 1187 | 5 | B | 110614 | |
| 1187 | 5 | C | 110616 | Yellow-Green |
| 1187 | 5 | D | 110617 | |
| | | | * * * | |
| 1187 | 6 | A | 110639 | |
| 1187 | 6 | B | 110644 | |
| 1187 | 6 | C | 110650 | Green |
| 1187 | 6 | D | 110652 | |
| | | | * * * | |
| 1187 | 7 | A | 110674 | |
| 1187 | 7 | B | 110676 | |
| 1187 | 7 | C | 110684 | Green |
| 1187 | 7 | D | 110685 | |
| | | | * * * | |
| 1187 | 8 | A | 110702 | |
| 1187 | 8 | B | 110707 | |
| 1187 | 8 | C | 110713 | Green |
| 1187 | 8 | D | 110716 | |
| | | | * * * | |
| 1187 | 9 | A | 110747 | |
| 1187 | 9 | B | 110749 | |
| 1187 | 9 | C | 110750 | Blue-Green |
| 1187 | 9 | D | 110760 | |
| | | | * * * | |
| 1187 | 10 | A | 110793 | |
| 1187 | 10 | B | 110803 | |
| 1187 | 10 | C | 110807 | Green |
| 1187 | 10 | D | 110809 | |
| | | | * * * | |
| 1187 | 11 | A | 110825 | |
| 1187 | 11 | B | 110836 | |
| 1187 | 11 | C | 110838 | Green |
| 1187 | 11 | D | 110841 | |
| | | | * * * | |
| 1188 | 5 | A | 110936 | |
| 1188 | 5 | B | 110940 | |
| 1188 | 5 | C | 110941 | Yellow |
| 1188 | 5 | D | 110945 | |
| | | | * * * | |
| 1188 | 9 | A | 111051 | |
| 1188 | 9 | B | 111052 | |
| 1188 | 9 | C | 111053 | Blue |
| 1188 | 9 | D | 111054 | |
| | | | * * * | |
| 1189 | 5 | A | 111249 | |
| 1189 | 5 | B | 111260 | |
| 1189 | 5 | C | 111261 | Yellow |
| 1189 | 5 | D | 111262 | |
| | | | * * * | |

The number of compounds in each test well can vary from 5 to 20, preferably 8–12/well or zone. Ten compounds per well may be an optimum number. If the number of compounds in each well is increased, the number of active wells will increase, and the number of compounds that need to be followed up increases exponentially. However, if three or more arrays (such as a "Z" plate) were used, then more compounds per well could be inserted. The Z plate could be arranged 90° from the "Y" plate for convenience.

Mathematically, the determination of a "hit" can be expressed as follows. Each compound involved in the screening can be uniquely represented by three variables (i,j,k), where k is the simple plate in which the compound is located, and i and j are the row and column, respectively, in which the compound is located in the kth simple plate. Using these variables, a matrix $S_k[i,j]$ representative of the compounds located on the kth simple plate can be formed. Thus, ten matrices can be formed for the embodiment using 800 compounds located on ten simple plates: $S_1[i,j]$, $S_2[i,j]$, ..., $S_{10}[i,j]$. Since eight rows and ten columns are employed on each simple plate in this embodiment, the variable i ranges from 1 to 8 and the variable j ranges from 1 to 10.

The X plate and Y plate are also represented by matrices, namely $X[i,j]$ and $Y[i,j]$. The $X[i,j]$ and $Y[i,j]$ matrices are based upon the matrix representation $S_k[i,j]$ of the compounds in the ten simple plates. Specifically, the ten compounds within the ith row and jth column of the X plate are represented by $S_j[i,1]$, $S_j[i,2]$, $S_j[i,3]$, ..., $S_j[i,10]$. Similarly, the ten compounds within the ith row and jth column of the Y plate are represented by $S_1[i,j]$, $S_2[i,j]$, $S_3[i,j]$, ..., $S_{10}[i,j]$.

As a result, it can be seen that the compound represented by (i,j,k) is located in row i, column k of the X plate, and in row i, column j of the Y plate. This means that a hit due to the compound located in row i, column j of the kth simple plate results in a hit in row i, column k of the X plate, and a hit in row i, column j of the Y plate. Inversely, a hit observed in row i, column k of the X plate and a hit in row i, column j of the Y plate is potentially due to the (i,j,k) compound.

Visually, when a hit is observed at a well in the Y plate, one can conclude that the hit resulted due to an active compound located at the same well location in one of the ten simple plates. A hit in the same row of the X plate can then be used to determine which of the ten simple plates contains the active compound. Specifically, the column number of the hit represents the simple plate which contains the active compound.

Pseudo-code for a procedure for determining the potentially active compounds is as follows.

Do for each row i=1, 2, . . . , 8:
 Let k1, k2, . . . be the column numbers of the hits in row i of X plate;
 Let j1, j2, . . . be the column numbers of the hits in row i of the Y plate;
 The potentially active compounds are (i,j1,k1), (i,j1,k2), (i,j2,k1), (i,j2,k2), . . . 10 simple plates: $S_1[i,j], S_2[i,j], \ldots, S_{10}[i,j]$ where
  i=1,2, . . . , 8
  j=1,2, . . . , 10
[i,j]:

[1, 1]  [1, 2]  [1, 3]  ...  [1, 10]

[2, 1]  [2, 2]  [2, 3]  ...  [2, 10]

[3, 1]  [3, 2]           .

⋮   ⋮            ⋮

[8, 1]  [8, 2]    ...    [8, 10]

For X plate:

$$x[i, j] = S_j[i, 1] + S_j[i, 2] + S_j[i, 3] + \ldots + S_j[i, 10]$$

$$= \sum_{k=1}^{10} S_j[i, k]$$

For Y plate:

$$y[i, j] = S_1[i, j] + S_2[i, j] + S_3[i, j] + \ldots + S_{10}[i, j]$$

$$= \sum_{k=1}^{10} S_j[i, k]$$

∴ code each compound as $(i, j, k) <--> S_k[i, j]$ $<-->$ row $i$, column $j$ of plate $k$ This compound is in:
row i, column k of X plate, and
row i, column j of Y plate.
=> Inversely, if there is a hit for x[i,j] and a hit for y[i,j], then the compound in $S_k[i,j]$ may be the cause.

The current technique for screening large numbers of compounds is applicable for a variety of screens, most preferably biological screenings. By a screen is meant a biological assay that is developed to determine the biological activity of a material.

The collection of materials that are available may be tested against an assay. In this fashion, it can be said that a database of materials can be screened for a particular assay to determine the activity of the portions of the database underneath the assay.

For example, an assay may be followed to determine if a material may be a cholesteryl ester transfer protein inhibitor (CETP). The test is described as follows.

CETP is a 74 kDa plasma glycoprotein responsible for the reciprocal exchange of neutral lipids between circulating lipoproteins. Net alteration in lipoprotein core lipid composition is a complex process. The modifications are influenced by lipoprotein concentration, lipoprotein residence time, and the activities of lecithin:cholesteryl acyl transferase (LCAT), hepatic lipase, lipoprotein lipase, and CETP. In general, in species lacking CETP activity, and humans genetically-deficient in CETP, the equilibrium favors elevation of anti-atherogenic (HDL) and diminution of atherogenic (LDL) lipoproteins. Therefore, plasma CETP inhibition could be an advantageous pharmacological target for the treatment of dyslipidemic patients at risk for coronary heart disease.

Recent studies of a Japanese family with deficiency in plasma CETP have shown that the deficiency was associated with marked elevation of HDL, its associated apolipoproteins (apoA-I, apoE, apoA-IV) and a rarity of coronary artery disease. The defect has been identified as a G (guanine) to A (adenine) substitution in the fourteenth intron of CETP pre-messenger RNA (ribonucleic acid). This splice donor defect is also the cause of the deficiency in additional Japanese families identified. In other studies, the deficiency (both homozygous and heterozygous) has been shown to be associated with a large proportion of Japanese with hyper-alphalipoproteinemia.

Also, a missense mutation at nucleotide 1506 (G for A) has been identified in exon 15 of the CETP gene, resulting in a substitution of a glycine for aspartic acid at amino acid 442. The two subjects heterozygous for the missense mutation had three times the normal HDL (high density lipoprotein) levels. Overall, these studies suggest that even partial reduction in CETP levels, as found in heterozygous individuals, is associated with elevated HDL. This apparently benign condition (CETP deficiency) has been coined the "longevity syndrome".

A variety of species, which lack CETP activity, including mice, rats, and dogs, have HDL as their major lipoprotein. When fed atherogenic diets, transgenic mice expressing human or cynomologus monkey CETP develop atherogenic lipoprotein profiles, including elevation of apoB containing lipoproteins (VLDL and β-VLDL) and reduction of HDL. These mice also develop atherosclerotic lesions. In the transgenic mice, CETP plasma activity has also been shown to be directly correlated with apoB and inversely correlated with apoA-I levels. Infusion of antibodies to CETP into rabbits results in a more favorable lipoprotein profile, including elevated HDL cholesterol and particle size. Conversely, infusion of CETP into rats results in a less favorable lipoprotein profile, including elevation of VLDL and LDL cholesterol and apoB, and diminution of apoE-rich HDL cholesterol and HDL size.

Preparation of CETP

The d>1.21 g/ml fraction was isolated from rabbit (Pel-Freez Biologicals, Rogers, Ark.) or human plasma and dialyzed against 50 mM Tris, 150 mM NaCl, 2 mM EDTA (ethylene diamine tetracetic acid), pH 7.4 buffer (1XDB, pH 7.4). Aliquots were stored frozen at −20° C. Chinese Hamster Ovary cells transfected with human recombinant CETP may be obtained by license agreement from Columbia University, New York. Media from these cells grown in 10% fetal bovine serum in Hams F-12 was used as a source of human CETP without further purification. The human CETP inhibitory monoclonal antibody TP2 (Mab TP2) may be obtained from Dr. Ross Milne and Yves Marcel (University of Ottawa Heart Institute). Mab TP2 is also known to inhibit rabbit CETP.

Radioisotopic Whole Plasma CETP Assays

Inhibitor screens were performed in 102.5 or 205 $\mu$l total volumes in deep 96-well polypropylene plates (1.2 ml capacity/well) or glass tubes, respectively. Compounds (final concentrations up to 100 $\mu$M) were added in 2.5 or 5.0 $\mu$l DMSO and pre-incubated for 1 hour at 37° C. with previously frozen human plasma (25 or 50 $\mu$l). $^3$H-CL-HDL$_3$ (20,000 or 40,000 dpm) in 75 or 150 $\mu$l of 1XDB, pH 8.0 was added and incubated at 37° C. Wells were harvested periodically up to 24 h by the addition of a 1.0 ml solution (per 102.5 $\mu$l incubation) containing 10 mg/ml bovine serum albumin, 1.29 mg/ml bovine intestinal mucosa heparin (Sigma Chemical Co., St. Louis, Mo.) in 0.14 M MnCl$_2$.4H$_2$O in 1XDB pH 8.0. Samples were mixed and after 10 minutes centrifuged at 2200 rpm for 30 minutes at 10° C. in an IEC PR-6000 centrifuge to precipitate apoB containing lipoproteins. Supernatant aliquots were counted by liquid scintillation spectroscopy to determine radioactivity remaining in HDL$_3$. See JOURNAL OF LIPID RESEARCH, Vol. 34, 1993, pp. 1625–1634, entitled "Use of Fluorescent Cholesteryl Ester Microemulsions and Cholesteryl Ester Transfer Protein Assays" by C. L. Bisgaier et al.

The invention herein may likewise be used in the spectrophotometric microtiter-based assay for the detection of hydroperoxy derivatives of linoleic acid. See, ANALYTICAL BIOCHEMISTRY, 201, 375–380 (1992) by B. J. Auerbach et al.

An assay for the detection of hydroperoxy derivatives of linoleic acid formed by the action of 15-lipoxygenase is described. The assay developed is based on a method first reported by Ohishi et al (1985) BIOCHEM. INT. 10, 205–211, with some modifications. The assay described herein takes advantage of the ability of (9Z,11E)-13-hydroperoxyoctadecadienoic acid (13-HPODE), the product of the action of 15-lipoxygenase on linoleic acid, to oxidize N-benzoyl leucomethylene blue to methylene blue in the presence of hemoglobin. The resultant blue color is stable to light and air and can be quantified spectrophotometrically at 660 nm. The linear range of the assay is 1.6–3.2 nmol (0.5–10 $\mu$g) of 13-DPODE. The utility of the assay can be extended to detect other peroxides as well as inhibitors of 15-lipoxygenase. The assay is a rapid, reliable method for the detection of lipid hydroperoxide production.

The methods and the materials utilized for this assay are as follows:

Materials. The following chemicals were purchased and used as received: linoleic acid (NuCheck Prep), 13(S)-HPODE, NDGA (nordihydroguaiaretic acid), ETYA (5,8,11,14-Eicosatetraynioc acid), 14,15-methano-LTA$_4$ (leukotriene A$_4$), (Biomol Research Labs), N-benzoyl leucomethylene blue (Tokyo Kasei Kogyo Co., Ltd.), dimethylformamide (DMF; Aldrich), sodium cholate, Triton X-100, 30% H$_2$O$_2$, 70% t-butyl hydroperoxide, and hemoglobin, bovine (Sigma). Probucol and indomethacin were prepared at Parke-Davis.

Methylene Blue Method For Peroxide Detection. The assay is performed in a 96-well microtiter plate. Each well contains 40 $\mu$l of substrate solution consisting of 160 $\mu$M linoleic acid, 5% ethanol, 0.2% sodium cholate in PBS without EDTA, inhibitor, if included, and 0.16 U enzyme isolated from phenylhydrazine-treated rabbit reticulocyte preparations (21) [1 U=1 nmol linoleic acid utilized/min at 4° C.] for a total volume of 50 $\mu$l. The plate is then incubated at 4° C. for 10 minutes followed by the addition of 100 $\mu$l of LMB color reagent consisting of 5 mg LMB dissolved in 8 ml DMF, which is then added to a 0.05 M potassium phosphate buffer (pH 5) containing 1.4 g Triton X-100 and 5.5 mg hemoglobin in a total volume of 100 ml. After 5 minutes at room temperature, the samples can be read at 660 nm on a microtiter plate reader. Under these conditions, approximately 20% of the substrate is converted to product.

HPLC (High Pressure Liquid Chromatography) Method For 13(S)-HPODE Detection. For verification of the assay, HPLC analysis of the products was performed after incubation under the above-described conditions. The assay is terminated by the addition of an equal volume HPLC mobile phase (acetonitrile:water:methanol:acetic acid, 350:250:150:1). The samples are then injected onto a C18 column (Perkin-Elmer) with conjugated dienes monitored at 235 nm and keto-derivatives at 270 nm. A postcolumn chemiluminescence reaction was utilized to detect hydroperoxy fatty acid derivatives.

The invention can likewise be used for determining the epidermal growth factor receptor kinase activity.

The present invention may be used as an assay for Acetylcholinesterase (AChE) activity. See, for example, the Ellman method (Ashour et al, 1987, ANAL. BIOCHEM. 166, 353–360).

The invention may equally be useful as a assay for mutant reverse transcriptase. This test is a determination of inhibitors of viral DNA polymerase and reverse transcriptase. See, VIROLOGY, 114, 52 (1981: entitled "Mechanism of Inhibition of Epstein-Barr Virus Replication" by A. K. Datta et al.

The present invention can be used in an RNA enzyme assay system. The assay is a commercially available assay from Amersham entitled "RNase H(3H)-SPA Enzyme Assay System".

The test is equally applicable for looking for inhibitors of Hepatitis B virus. A typical technique is called Hepatitis B virus reverse transcriptase assay. The assay procedure is a commercially available assay procedure.

The invention is equally applicable to detect HIV protease enzyme. There is a commercially available testing identified as Amersham's HIV protease $^{125}$I-SPA assay system.

The invention is equally applicable to determining the ability of materials for rust-removing activity, or the ability to dye various textile materials, or the ability to clean substrates, or the ability of material to decompose in the presence of bacteria such as soiled bacteria and the like.

The invention is equally applicable to determining a compound's ability to hybridize to a library of genes, or whether particular materials are sensitive to mammals and the like.

The invention is equally applicable to determining sunscreening activity or immune response in mammals. Various Elisa (enzyme link immuno sorbant activity) which enzyme can detect for the presence of a number of biologic materials such as various components of the blood such as T-cells, B-cells, interleukins, and the like.

The invention is equally applicable for determining the presence or absence of a gene which is associated with a particular malady or a gene that is associated with an absence of a biological response in mammals. The test could be applicable for determining the permeability of materials to a membrane such as a cellular membrane. The test is applicable for determining the activity of a cell to transduce signals over the ability of different materials to bind two cells or to bind enzymes or antibodies. See, CELLULAR AND MOLECULAR IMMUNOLOGY (2nd Edition) 1994 by A. K. Abbas, pp. 56–60.

It is to be appreciated that a wide variety of a compound's activities could be determined such as:

- the activity to be tested of the compounds is a rust remover activity;
- the activity is the ability to dye textile materials;
- the activity is to clean substrates;
- the activity is the ability to decompose in the presence soil bacteria;
- the activity is the ability of compounds to hybridize to a library of genes;
- the activity is the ability to detect sun screen activity; the sun screens are also detected for sensitivity to mammals;
- the activity is the ability to induce an immune response in mammals;
- the activity is presence of a gene associated with a malady;
- the activity is absence of a gene associated with a malady;
- the activity is presence of a gene associated with a biological response in mammals;
- the activity is the absence of a gene associated with a biological response in mammals;
- the activity is permeability of a membrane;
- the activity is effecting a signal transduction of a cell;
- the activity is ability to bind to a cell;
- the activity is ability to bind to an enzyme; and
- the activity is ability to bind to an antibody.

The present invention is equally applicable to determining an optimized dosage or weight for active compounds. In other words, the present invention can assist in quantitatively determining active materials and their degree of activity. In this manner, identical or differential amounts of a compound(s) to be tested are placed in various unique well locations.

For a discussion of applicability of the present invention to the simultaneous synthesis of compositions, reference may be made to the concurrently filed patent application entitled "A Method for the Synthesis of Mixtures of Compounds" commonly owned, attorney's case #PD5116, Ser. No. 08/923,801, hereby incorporated by reference.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A method of simultaneously testing a plurality of compounds for activity in a screen which is a biological assay to determine the biological activity of the compounds comprising the steps of:

(a) placing a plurality of the compounds into a solvent for the compounds into at least two arrays, each having a plurality of test zones, with multiple compounds in each zone and at least one identical compound in at least two arrays;

(b) determining the array location of each compound in each test zone;

(c) testing the compounds in the solvent for activity in the biological assay thereby subjecting the arrays to the biological assay testing screen; and ascertaining the compounds that had a positive response to the biological assay testing screen.

2. The method of claim 1 wherein at least one identical compound to be tested is placed in each array.

3. The method of claim 1 wherein there are more than two arrays.

4. The method of claim 1 wherein there are at least three arrays.

5. The method of claim 1 wherein the activity is the ability to decompose in the presence of soil bacteria.

6. The method of claim 1 wherein the activity is the ability of compounds to hybridize to a library of genes.

7. The method of claim 1 wherein the zones contain variations in the concentration of compounds tested.

8. The method of claim 1 wherein the activity is the ability to induce an immune response in mammals.

9. The method of claim 1 wherein the activity is presence of a gene associated with a malady.

10. The method of claim 1 wherein the activity is absence of a gene associated with a malady.

11. The method of claim 1 wherein the activity is presence of a gene associated with a biological response in mammals.

12. The method of claim 1 wherein the activity is the absence of a gene associated with a biological response in mammals.

13. The method of claim 1 wherein the activity is permeability of a membrane.

14. The method of claim 1 wherein the activity is effecting a signal transduction of a cell.

15. The method of claim 1 wherein the activity is ability to bind to a cell.

16. The method of claim 1 wherein the activity is ability to bind to an enzyme.

17. The method of claim 1 wherein the activity is ability to bind to an antibody.

18. The method of claim 1 wherein the activity is to determine a cholesteryl ester transfer protein inhibitor.

19. The method of claim 1 wherein the activity is a kinase activity.

20. The method of claim 1 wherein the activity is an epidermal growth factor receptor kinase inhibitor.

21. The method of claim 1 wherein the activity is an acetylcholinesterase activity.

22. The method of claim 1 wherein the activity is a reverse transcriptase activity.

23. The method of claim 1 wherein the activity is a ribonucleic acid enzyme assay activity.

24. The method of claim 1 wherein the activity is a hepatitis B virus inhibitor.

25. The method of claim 1 wherein the activity is a human immunovirus protease enzyme.

26. The method of claim 1 wherein the activity is a human immunovirus protease activity.

27. The method of claims 1 or 2 wherein the number of compounds to be tested in each test zone ranges from 5 to 20 per zone.

28. The method of claims 1 or 2 wherein the number of compounds to be tested in each test zone ranges from 8 to 12 per zone.

29. The method of claim 1 further comprising ascertaining a quantitative determination of compound activity by placing in different test zones identical or differential amounts of compounds being tested.

* * * * *